(12) United States Patent
Knoll et al.

(10) Patent No.: US 10,671,939 B2
(45) Date of Patent: Jun. 2, 2020

(54) SYSTEM, METHOD AND COMPUTER-ACCESSIBLE MEDIUM FOR LEARNING AN OPTIMIZED VARIATIONAL NETWORK FOR MEDICAL IMAGE RECONSTRUCTION

(71) Applicants: NEW YORK UNIVERSITY, New York, NY (US); Graz University of Technology, Graz (AT)

(72) Inventors: Florian Knoll, New York, NY (US); Kerstin Hammernik, Graz (AT); Thomas Pock, St. Radegund (AT); Daniel K. Sodickson, Larchmont, NY (US)

(73) Assignees: New York University, New York, NY (US); Graz University of Technology, Graz (AT)

( * ) Notice: Subject to any disclaimer, the term of this patent is extended or adjusted under 35 U.S.C. 154(b) by 304 days.

(21) Appl. No.: 15/495,511

(22) Filed: Apr. 24, 2017

(65) Prior Publication Data
US 2017/0309019 A1 Oct. 26, 2017

Related U.S. Application Data

(60) Provisional application No. 62/326,169, filed on Apr. 22, 2016.

(51) Int. Cl.
*G06N 20/00* (2019.01)
*G06T 5/00* (2006.01)
(Continued)

(52) U.S. Cl.
CPC ......... *G06N 20/00* (2019.01); *G01R 33/5611* (2013.01); *G06T 5/00* (2013.01);
(Continued)

(58) Field of Classification Search
CPC ... G06N 20/00; G01R 33/5611; G06T 11/006; G06T 7/00; G06K 9/00
See application file for complete search history.

(56) References Cited

U.S. PATENT DOCUMENTS

| | | | | |
|---|---|---|---|---|
| 2015/0287223 A1* | 10/2015 | Bresler | ................. | G06T 11/006 382/131 |
| 2016/0341810 A1* | 11/2016 | Rich | ................... | G01R 33/5608 |
| 2017/0109881 A1* | 4/2017 | Avendi | ................... | G06T 7/0012 |

OTHER PUBLICATIONS

Wang, Shanshan "Accelerating Magnetic Resonance Imaging VIADeep Learning" IEEE 13th International Symposium on Biomedical Imaging. Apr. 13-16, 2016. (Year: 2016).*

(Continued)

*Primary Examiner* — Kim Y Vu
*Assistant Examiner* — Molly Delaney
(74) *Attorney, Agent, or Firm* — Hunton Andrews Kurth LLP

(57) ABSTRACT

An exemplary system, method and computer accessible medium for generating an image(s) of a portion(s) of a patient can be provided, which can include, for example, receiving first imaging information related to the portion(s), receiving second information related to modelling information of a further portion(s) of a further patient(s), where the modelling information includes (i) an under sampling procedure, and/or (ii) a learning-based procedure, and generating the image(s) using the first information and the second information. The modelling information can include artifacts present in a further image of the further portion(s). The image(s) can be generated by reducing or minimizing the artifacts. The second information can be generated, for example using a variational network(s).

34 Claims, 12 Drawing Sheets

(51) Int. Cl.
G06T 11/00 (2006.01)
G01R 33/561 (2006.01)
G01R 33/48 (2006.01)

(52) U.S. Cl.
CPC ........ *G06T 11/006* (2013.01); *G01R 33/4824* (2013.01); *G06T 2207/10088* (2013.01); *G06T 2207/20081* (2013.01)

(56) References Cited

OTHER PUBLICATIONS

Lustig, Michael et al., "Sparse MRI: The Application of Compressed Sensing for Rapid MR Imaging," Magnetic Resonance in Medicine, vol. 58, pp. 1182-1195, 2007.
Block, Kai Tobias et al., "Undersampled Radial MRI with Multiple Coils. Iterative . . . ," Magnetic Resonance in Medicine, vol. 57, pp. 1086-1098, 2007.
Ma, Dan et al., "Magnetic Resonance Fingerprinting," Nature, vol. 495, No. 7440, pp. 187-192, Mar. 14, 2013.
Chen, Yunjin et al., "On Learning Optimized Reaction Diffusion Processes . . . ," IEEE Conference on Computer Vision and Pattern Recognition, pp. 5261-5269, 2015.
Bilgic, Berkin et al., "Multi-Contrast Reconstruction with Bayesian Compressed Sensing," Magn Reson Med., vol. 66, No. 6, pp. 1601-1615, Dec. 2011.
Sumpf, Tilman J. et al., "Fast T2 Mapping with Improved Accuracy Using Undersampled . . . ," IEEE Trans Med Imaging, vol. 33, No. 12, pp. 2213-2222, Dec. 2014.
Doneva, Mariya et al., "Compressed Sensing Reconstruction for Magnetic Resonance Parameter Mapping," Magnetic Resonance in Medicine, vol. 64, pp. 1114-1120, 2010.
Keeling, Stephen L. et al., "A Total Variation Based Approach to Correcting Surface . . . ," Applied Mathematics and Computation, vol. 218, pp. 219-232, 2011.
Sodickson, D.K. et al., "The Rapid Imaging Renaissance: Sparser Samples, Denser Dimensions . . . ," vol. 9417, SPIE, pp. 1-15, 2015.
Cloos, Marijn A. et al., "Magnetic Resonance Fingerprint Compression," Proc. Intl. Soc. Mag. Reson. Med., No. 23, p. 330, 2015.
Pruessman, Klaas P. et al., "Advances in Sensivity Encoding with Arbitary k-Space Trajectories," Magnetic Resonance in Medicine, vol. 46, pp. 638-651, 2001.
Huang, Jinggang et al., "Statistics of Natural Images and Models," In Proceedings of the IEEE Conference on Computer Vision and Pattern Recognition, pp. 541-547, 1999.
Zhu, Song Chun et al., "Prior Learning and Gibbs Reaction . . . ," IEEE Transaction of Pattern Analysis and Machine Intelligence, vol. 19, No. 11, pp. 1236-1250, Nov. 1997.
Block, Kai Tobias et al., "Model-Based Iterative Reconstruction for Radial Fast Spin-Echo MRI," IEEE Transactions on Medical Imaging, vol. 28, No. 11, pp. 1759-1769, Nov. 2009.

* cited by examiner

TV value: 4499     TV value: 6274     TV value: 8281

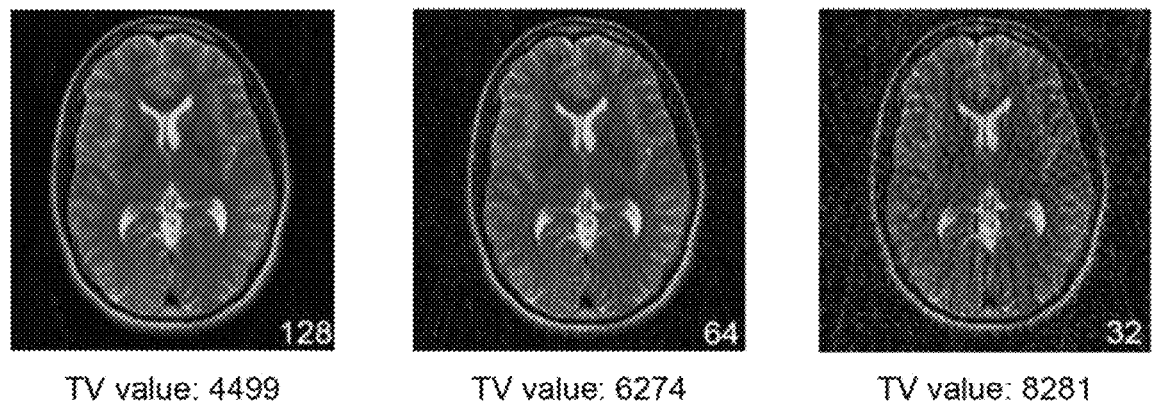
Figure 5
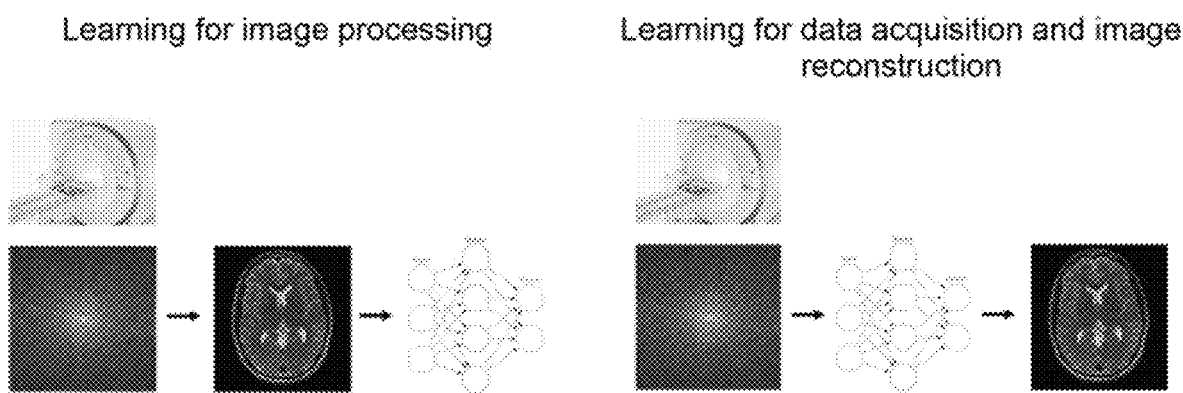
Figure 6A
Figure 6B

SYSTEM, METHOD AND COMPUTER-ACCESSIBLE MEDIUM FOR LEARNING AN OPTIMIZED VARIATIONAL NETWORK FOR MEDICAL IMAGE RECONSTRUCTION

CROSS-REFERENCE TO RELATED APPLICATION(S)

This application relates to and claims priority from U.S. Patent Application No. 62/326,169, filed on Apr. 22, 2016, the entire disclosure of which is incorporated herein by reference.

STATEMENT REGARDING FEDERALLY SPONSORED RESEARCH

This invention was made with government support under Grant Nos. R01 EB000447 and P41 EB017183, awarded by the National Institute of Health. The government has certain rights in the invention.

FIELD OF THE DISCLOSURE

The present disclosure relates generally to image reconstruction, and more specifically, to exemplary embodiments of an exemplary system, method and computer-accessible medium for learning an optimized variational network for medical image reconstruction.

BACKGROUND INFORMATION

Compressed Sensing ("CS") procedures facilitate Magnetic Resonance Image ("MRI") reconstruction from undersampled k-space data. Existing methods are based on simple regularizers such as Total Variation ("TV") (see, e.g., Reference 1) or sparsity in the wavelet domain. (See, e.g., Reference 2). However, these handcrafted models are too simple to capture the characteristic structure of complex anatomies. Additionally, application of CS in clinical practice is still challenging due to expensive computations, parameter selection and limited applicability to two-dimensional ("2D") Cartesian protocols.

Thus, it may be beneficial to provide an exemplary system, method, and computer accessible medium for learning an optimized variational network, which can overcome at least some of the deficiencies described herein above.

SUMMARY OF EXEMPLARY EMBODIMENTS

An exemplary system, method and computer accessible medium for generating an image(s) of a portion(s) of a patient can be provided, which can include, for example, receiving first imaging information related to the portion(s), receiving second information related to modelling information of a further portion(s) of a further patient(s), where, for example, the modelling information includes at least one of (i) an undersampling procedure or (ii) a learning-based procedure, and generating the image(s) using the first information and the second information. The modelling information can include artifacts present in a further image of the further portion(s). The image(s) can be generated by reducing or minimizing the artifacts. The second information can be generated, for example using a variational network(s).

In some exemplary embodiments of the present disclosure, the variational network(s) can be based on a gradient descent procedure(s). The variational network(s) can be based on a loss function. The loss function can be minimized over a set of training images of the further portion(s). The undersampling procedure and/or the learning-based procedure can include filter kernels and corresponding influence functions of the variational network(s). The filter kernels and influence functions can be learned by optimizing a loss function that can compare undersampled, aliased, images to artifact-free reference reconstructions of the portion(s). The variational network(s) ca includes convolutional filters in a real plane and/or an imaginary plane. Errors in the first imaging information can be removed using the second information.

The image(s) can be generated by applying the second imaging information to the first imaging information. The undersampling procedure and/or the learning-based procedure can be generated. The undersampling procedure and/or the learning-based procedure can be generated by using information about a pattern in k-space in the second imaging information to discriminate aliasing artifacts. The aliasing artifacts can be based on undersampling from true anatomical structures. The undersampling procedure and/or the learning-based procedure can be generated based on coil sensitivities and raw k-space measurement in the second imaging information. The first imaging information and/or the second imaging information can include (i) magnetic resonance imaging information, (ii) computed tomography imaging information, (iii) positron emission tomography imaging information, and/or (iv) optical imaging information.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which:

FIG. 5 is a set of exemplary images illustrating the effect of antialiasing according to an exemplary embodiment of the present disclosure;

FIG. 6A is a diagram illustrating a conventional learning for an image processing procedure for image reconstruction;

FIG. 6B is an exemplary diagram illustrating the exemplary learning for data acquisition and image construction procedure according to an exemplary embodiment of the present disclosure;

Figure 1:
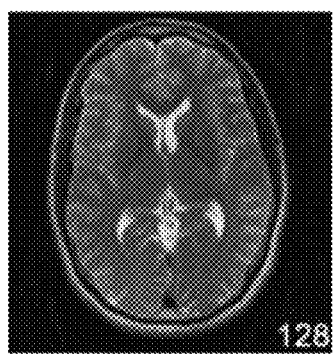
FIG. 1 is a set of exemplary images of an anatomical structure showing artifacts and the corresponding Total Variation functional value.
Figure 1:
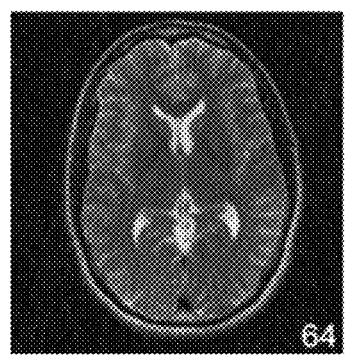
Figure 1:
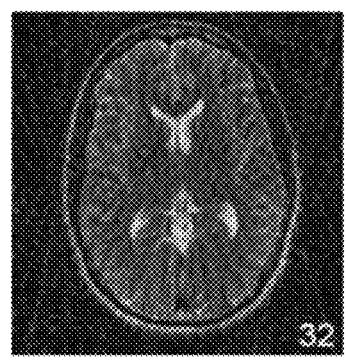

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

As described herein below, the exemplary system, method and computer-accessible medium, according to an exemplary embodiment of the present disclosure, can utilize a MRI reconstruction procedure by learning optimal regularization that can effectively avoid undersampling artifacts, while also preserving the natural image appearance. To overcome various limitations and/or deficiencies of previous capital MRI reconstruction procedures, the exemplary system, method and computer-accessible medium can learn a set of filters, and corresponding penalty functions, of a variational model.

Significant improvements in terms of acquisition time and image quality were reported over the last few years due to advanced data acquisition and reconstructions methods such as CS (see, e.g., Reference 1), the resurgence of non-Cartesian imaging (see, e.g., Reference 2) and most recently magnetic resonance ("MR") fingerprinting. (See, e.g., Reference 3). In CS, reconstruction of accelerated images can be achieved with an iterative method that can solve an optimization problem of the following exemplary form:

$$\min \frac{1}{2}\|Au-f\|_2^2 + \lambda \|\Psi(u)\|_1 \quad (1)$$

In Eq. (1), u can be the current image estimate, A can be the operator that can map between data space and image space and $\Psi$ can be the regularization functional that can separate between true image content and aliasing artifacts caused by undersampling (e.g., wavelets and the TV semi norm can be commonly used). The $l_1$ norm in the regularization term can be beneficial to promote a solution that can separate between sparse image content and incoherent aliasing artifacts due to undersampling.

FIG. 1 shows a set of exemplary images of a typical streak-structure of aliasing artifacts for a radially undersampled MR brain acquisition. The corresponding numerical TV values (e.g., arbitrary units) are also shown. The TV value can increase together with increased aliasing as the amount of data can be reduced. This can illustrate that the functional can detect image corruption by aliasing artifacts. Therefore, the role of the regularization functional in Eq. (1) can be to promote solutions where artifacts can be reduced. However, with current methods, improvements can be shown for specialized research applications like four-dimensional ("4D") cardiovascular imaging, three-dimensional ("3D") non-Cartesian acquisitions, functional-MRI, flow imaging or dynamic contrast enhanced MM. The vast majority of clinical routine exams currently do not use these procedures. Various reasons that hold back the widespread use of compressed sensing accelerated imaging in clinical practice include: (i) only moderate performance can be achieved for regular clinical 2D Cartesian imaging protocols, which form the cornerstone of all imaging exams, (ii) handcrafted sparsifying transforms and image models like TV or wavelets can be too simple to capture the characteristic structure of complex anatomies, which often leads to unnatural looking images, (iii) lack of robustness due to the need of tuning free parameters individually for certain exams, and (iv) prolonged reconstruction times.

Figure 2:
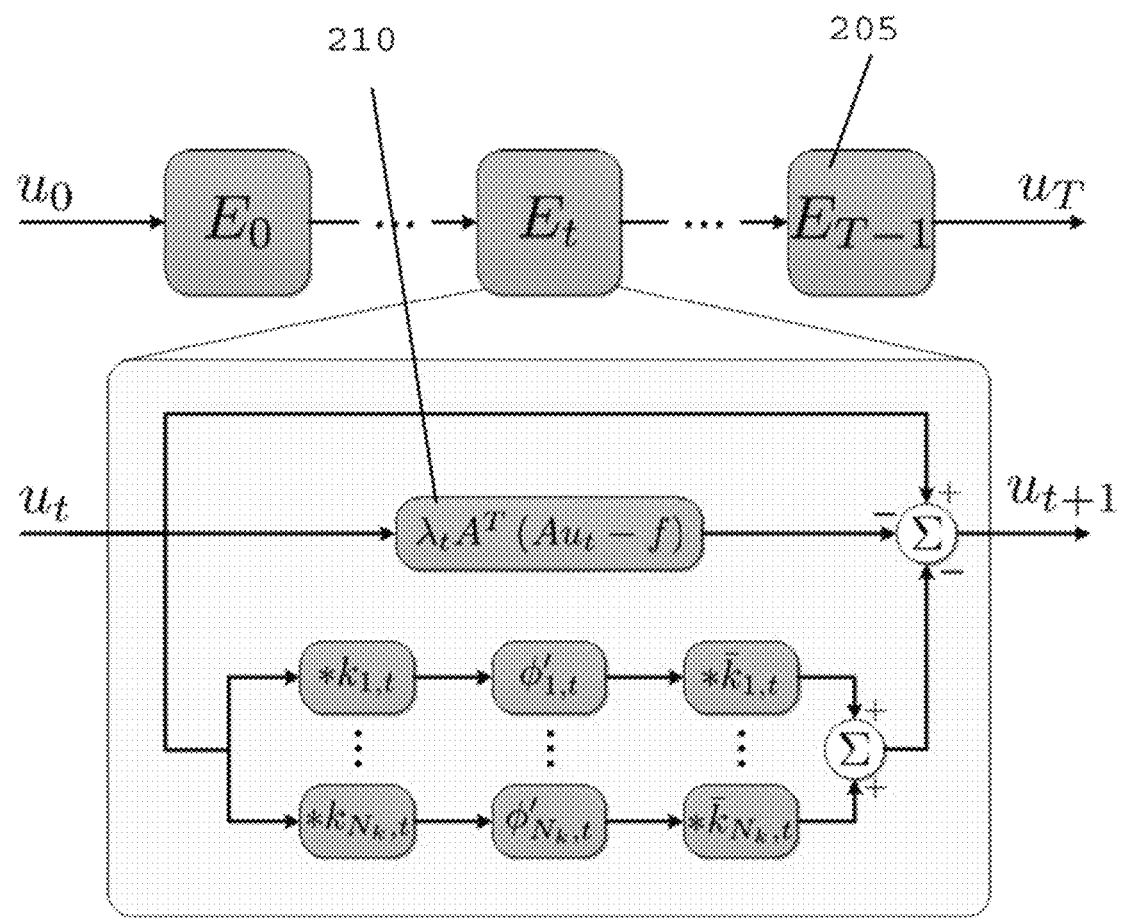
FIG. 2 is a block diagram of an exemplary variational network structure according to an exemplary embodiment of the present disclosure.

The exemplary variational network procedure is shown in the schematic diagram of FIG. 2. For example, as shown in the block diagram of FIG. 2, to reconstruct an image $u_T$, the image $u_0 = A^T f$ can be propagated through T steps of the variational network, which can correspond, to quadratic energies $E_t$ (e.g., element 205 of FIG. 2). During an exemplary training process, optimal filter kernels $k_{i,t}$, the derivatives of penalty functions $\varnothing'_{i,t}$ and the regularization parameter $\lambda_t$ (e.g., element 210 of FIG. 2) can be learned for each updated procedure.

The exemplary system, method and computer-accessible medium, according to an exemplary embodiment of the present disclosure, can reconstruct images rooted in machine learning and computer vision that can provide a solution to various problems presented in previous systems. Picture archiving and communication systems ("PACS") systems can archive hundreds of thousands of clinical data sets, but despite this wealth of information, every new image reconstruction procedure can be performed as if there is no information about the imaged anatomy. By reformulating image reconstruction as an optimized variational network, the exemplary system, method and computer-accessible medium, according to an exemplary embodiment of the present disclosure, can learn a complete reconstruction procedure, including filter kernels, and penalty functions to separate between true image content and artifacts, all parameters that normally have to be tuned manually, as well as the associated numerical procedure. The exemplary training procedure can be decoupled from the time critical image reconstruction procedure, which can then be performed in near real time without interruption of clinical workflow.

Figure 3:
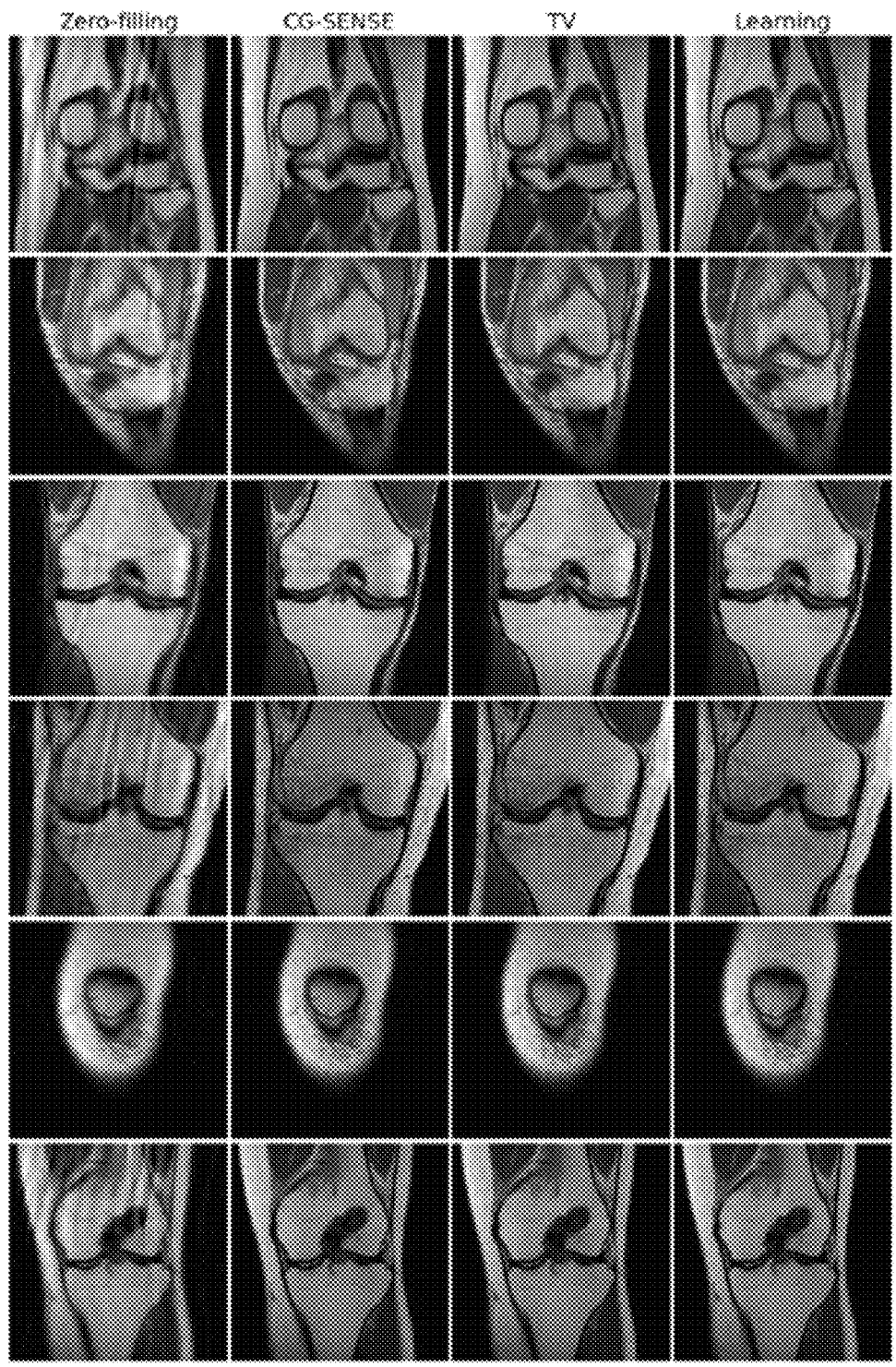
FIG. 3 is a set of exemplary images comparing previous image reconstruction methods against those generated by the exemplary system, method and computer-accessible medium according to an exemplary embodiment of the present disclosure.

FIG. 3 shows a set of exemplary images comparing to those generated by the exemplary system, method and computer-accessible medium to previous procedures for selected slices from 6 different patients undergoing knee MRI exams with an acceleration factor of R=2. Exemplary results were compared to one of the current standards in clinical practice, CG-SENSE (see, e.g., Reference 12), as well as one of the current standards in research, TV based combined parallel imaging and CS. (See, e.g., Reference 2). Conventional zero filling results can also be shown which can illustrate the amount of aliasing artifacts generated at this level of acceleration.

Figure 4:
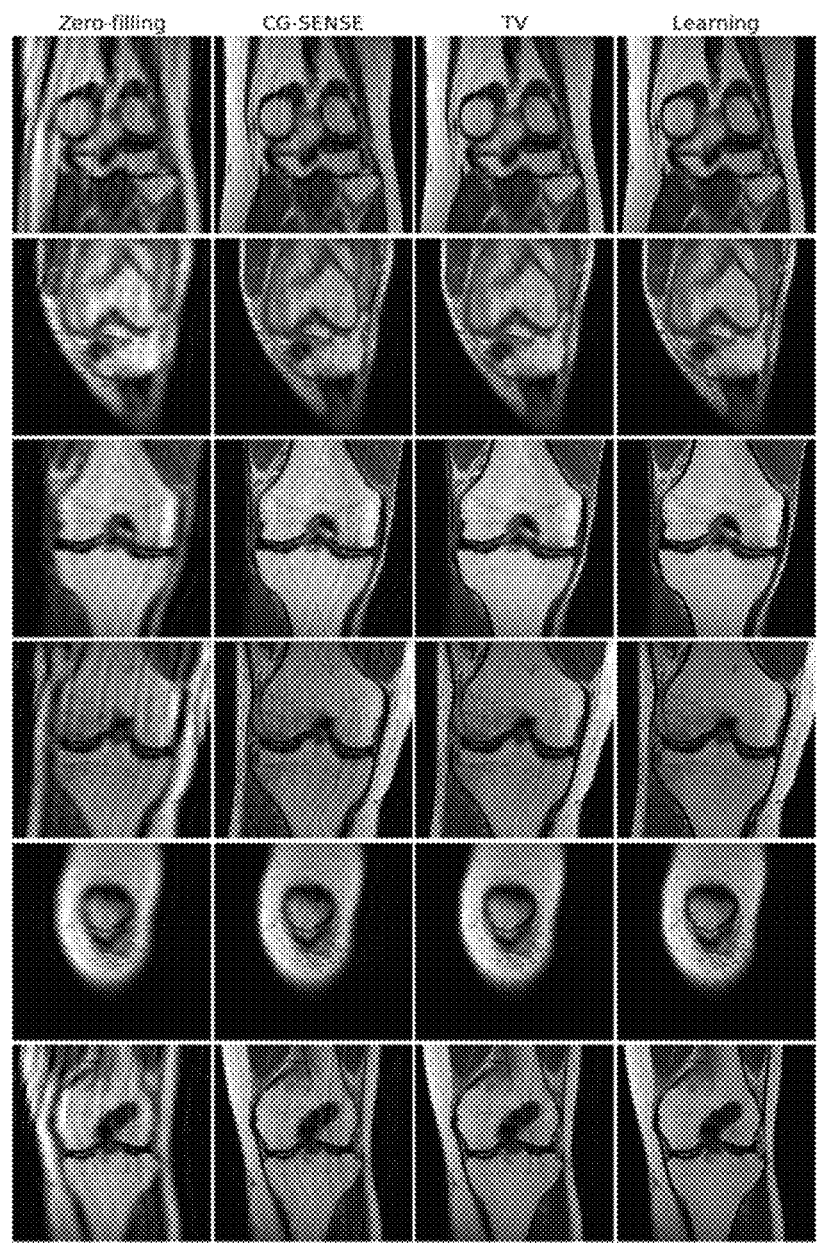
FIG. 4 is a further set of exemplary images with higher data acquisition speed than those in FIG. 3 comparing previous image reconstruction methods against those generated by the exemplary system, method and computer-accessible medium according to an exemplary embodiment of the present disclosure.

FIG. 4 shows a set of exemplary images comparing previous image reconstruction methods against those generated by the exemplary system, method and computer-accessible medium for an acceleration factor of R=6, according to an exemplary embodiment of the present disclosure. Each slice can be taken from a different patient. CG-SENSE (See, e.g., Reference 12) and CS using TV (See, e.g., References 1 and 2) show residual aliasing artifacts while the results of the exemplary system, method and computer-accessible medium can be artifact free. In addition, for example, the TV result shows the characteristic blocky appearance caused by the handcrafted regularization functional, as well as a slightly blurrier appearance with loss of small low contrast structures.

In contrast to current accelerated reconstruction methods like CS, the exemplary system, method and computer-accessible medium, according to an exemplary embodiment of the present disclosure, can utilize regularization functions that can separate artifacts from true image content, which can be specifically learned instead of using handcrafted and fixed sparsifying transforms.

Instead of relying purely on artifact incoherence, which needs major modifications to the data acquisition strategy, the exemplary system, method and computer-accessible medium can be directly applied to data from conventional parallel imaging based acquisition procedures. Thus, the clinical translation of the exemplary system, method and computer-accessible medium can be significantly easier than for previous CS based procedures.

The exemplary system, method and computer-accessible medium, according to an exemplary embodiment of the present disclosure, can have the accelerated MR imaging closer to daily clinical practice in areas that can be untouched by recent developments. This can reduce overall exam times, increase patient compliance and has the potential to reduce general healthcare costs.

The exemplary system, method and computer-accessible medium, according to an exemplary embodiment of the present disclosure, can have the following exemplary advantages. For example, reconstructed images can have a more natural appearance and fewer artifacts than current state of the art CS reconstructions. Faster data acquisition can lead to increased patient compliance, reduced motion artifacts and higher throughput, which can all lead to reduced healthcare costs. In particular, according to the exemplary preliminary data from clinical 2D knee protocols, data acquisition can be performed up to 6-times faster in comparison to a fully sampled scan. By inspecting the penalty functions and filter kernels of the learned variational network, the exemplary system, method and computer-accessible medium can be used as a discovery tool for sparsifying transforms and numerical methods for regular CS type reconstructions.

Exemplary Methods

The exemplary system, method and computer-accessible medium, according to an exemplary embodiment of the present disclosure, can generate a sequence $\{u_t\}$, $t=0 \ldots T-1$ of reconstructed images by minimizing a sequence of simple quadratic energies $\{E_t\}$, where, for example:

$$u_{t+1} = \arg\min_u E_t(u, \theta_t) = \arg\min_u <s_t(u_t), u - u_t> + \tfrac{1}{2}\|u - u_t\|_2^2, \quad (2)$$

where $s_t(u_t)$ can be learned functions defined below. The minimizers of the quadratic energies can form a gradient procedure with gradients $s_t(u_t)$, where, for example:

$$u_{t+1} = u_t - s_t(u_t). \quad (3)$$

Functions $s_t(u_t)$ can be defined as gradients of following exemplary variational model:

$$E_t(u) = \frac{\lambda_t}{2} \|Au - f\|_2^2 + \Sigma_{i=1}^{N_k} \varnothing_{i,t}(k_{i,t} * u). \quad (4)$$

The first term can enforce data consistency to measured k-space data fusing the linear forward sampling operator A that can implement pointwise multiplications with coil sensitivity profiles and Fast Fourier Transforms ("FFTs"). The second (e.g., regularization) term can convolve the image u with $N_k$ filter kernels $k_{i,t}$ and then can apply differentiable penalty functions $\varnothing_{i,t}$. The influence of both terms can be controlled via a regularization parameter $\lambda_t$. $s_t(u_t)$ can be defined as gradients of the variational model, where, for example:

$$s_t(u_t) = \nabla E_t(u)|_{u=u_t} = \lambda_t A^T(Au_t - f) + \Sigma_{i=1}^{N_k} \bar{k}_{i,t} * \varnothing'_{i,t}(k_{i,t} * u_t), \quad (5)$$

where $A^T$ can denote the backward operator, which can perform inverse FFTs and a combination of coil images, $\bar{k}_{i,t}$ can denote the filter kernels $k_{i,t}$ rotated by 180° and $\varnothing'_{i,t}$ can be the first derivative of the penalty functions. Thus, the exemplary system, method and computer-accessible medium can utilize a specialized convolutional neural network, performing a fixed number of learned gradient descent procedures starting from an initial solution $u_0$. (See, e.g., images shown in FIG. 1).

To learn the parameters of the exemplary network, the following loss function can be minimized over a set of S training images. For example:

$$\min_\theta \tfrac{1}{2} \Sigma_{s=1}^{S} \|u_{T,s}(\theta) - g_s\|_2^2, \quad (6)$$

where $u_{T,s}$ can denote the output of the network after T steps and $g_s$ can denote the reference images. The vector $\theta = \{\lambda_t, k_{i,t}, \varnothing_{i,t}, i=1 \ldots N_k, t=0 \ldots T-1\}$ can hold all unknown parameters of the exemplary network. After training, the exemplary learned network can be efficiently applied to new k-space data as it can perform only T steps of simple operations.

Exemplary System Setup 10 knee patients were scanned on a clinical 3T system (e.g., Siemens Magnetom Skyra) using a 15-channel knee coil. A coronal proton density ("PD") weighted Cartesian 2D turbine spin-echo sequence was used with following exemplary sequence parameters: TR=2690 ms, TE=33 ms, matrix size 320×320, 0.4×0.4 mm², 34 3 mm slices, acceleration factor R=2. This clinical protocol can deliver reference images without aliasing by using conventional parallel imaging ("PI") reconstruction from the scanner vendor.

The training was conducted on a subset of 40 images from 4 different patients. This data was additionally undersampled for an acceleration factor of R=6. An exemplary training procedure, and parameter initialization of the network, was performed. 48 filters of size 7×7 were trained; the corresponding penalty functions and the regularization parameter $\lambda_t$ for each of T=15 steps.

FIG. 5 shows a set of exemplary images illustrating the streak-structure of aliasing artifacts for a radially undersampled MR brain acquisition. The corresponding numerical TV values (e.g., arbitrary units) are also shown. The exemplary TV value can increase together with increased aliasing as the amount of data can be reduced. This illustrates that the functional can detect image corruption by aliasing artifacts. The corruption by characteristic streaking artifacts gets worse as the number of projections can be reduced from 128 to 64 and 32. At the same time, the value of the TV functional can increase, illustrating that the functional can detect image corruption by aliasing artifacts. Therefore, the role of the regularization functional in Eq. (1) can be to promote solutions where artifacts can be reduced.

The exemplary system, method and computer-accessible medium, according to an exemplary embodiment of the present disclosure, can be used to accelerate MR data acquisition utilizing undersampling and learning-based reconstruction. In contrast to learning for image processing (see, e.g., Reference 16), learning already at the data acquisition and image formation stage can be used.

The exemplary system, method and computer-accessible medium, according to an exemplary embodiment of the present disclosure, can be used to reconstruct images by formulating a dedicated variational network. Exemplary training can be performed by using information about the sampling pattern in k-space to discriminate aliasing artifacts due to undersampling from true anatomical structures. Coil sensitivities and raw k-space measurement data can be used as the input of the exemplary network, while the output can be the reconstructed image. Exemplary parameters, such as filter kernels and corresponding influence functions of the optimized variational network, can be learned to achieve the exemplary discrimination. The exemplary parameters can be learned by optimizing a loss function that can compare undersampled, aliased, images to artifact-free reference reconstructions.

The exemplary system, method and computer-accessible medium, according to an exemplary embodiment of the present disclosure, can use a network with convolutional filters in the real and imaginary plane in order to process complex natured MRI data. In contrast to iterative procedures, where every reconstruction can be handled as an individual optimization approach, the computationally expensive optimization procedure in the exemplary training procedure can be learned. New data can then simply be processed by passing the data through the network with the learned parameters.

The exemplary reconstruction procedure can be utilized to achieve an efficient GPU implementation that can facilitate the reconstruction of images without disrupting regular clinical workflow. An exemplary of the advantage of the exemplary system, method and computer-accessible medium, as compared to other previous approaches, is that the exemplary approach can be trained with a comparably low number of training cases. The results that were obtained for this disclosure were trained from only 10 cases. This can be beneficial for medical image reconstruction, since availability of training data can be restricted in comparison to tasks like image categorization or general image restoration.

The exemplary system, method and computer-accessible medium, according to an exemplary embodiment of the present disclosure, can be applied to both 2D and 3D anatomical imaging of a single contrast as well as dynamic imaging, different data acquisition trajectories, multi-contrast image reconstruction (see, e.g., Reference 17), quantitative imaging (see, e.g., References 18, 19, and 20, inhomogeneity correction (see, e.g., Reference 9), and advanced concepts like MR-Fingerprinting. (See, e.g., References 15, 22, and 23).

While the examples provided herein can be from MR image reconstruction, the exemplary system, method and computer-accessible medium, according to an exemplary embodiment of the present disclosure, can be applied to other imaging modalities, including, but not limited to, CT, PET or optical imaging.

The difference between using machine learning for image processing to image reconstruction in radiology is shown in the diagrams of FIGS. 6A and 6B. For example, the images shown in FIG. 6A are generated by improving the image quality after the image acquisition. The exemplary system, method and computer-accessible medium, can be used to improve the image acquisition (see, e.g., FIG. 6B), which can provide a superior image than just improving an already generated image.

Figure 7:
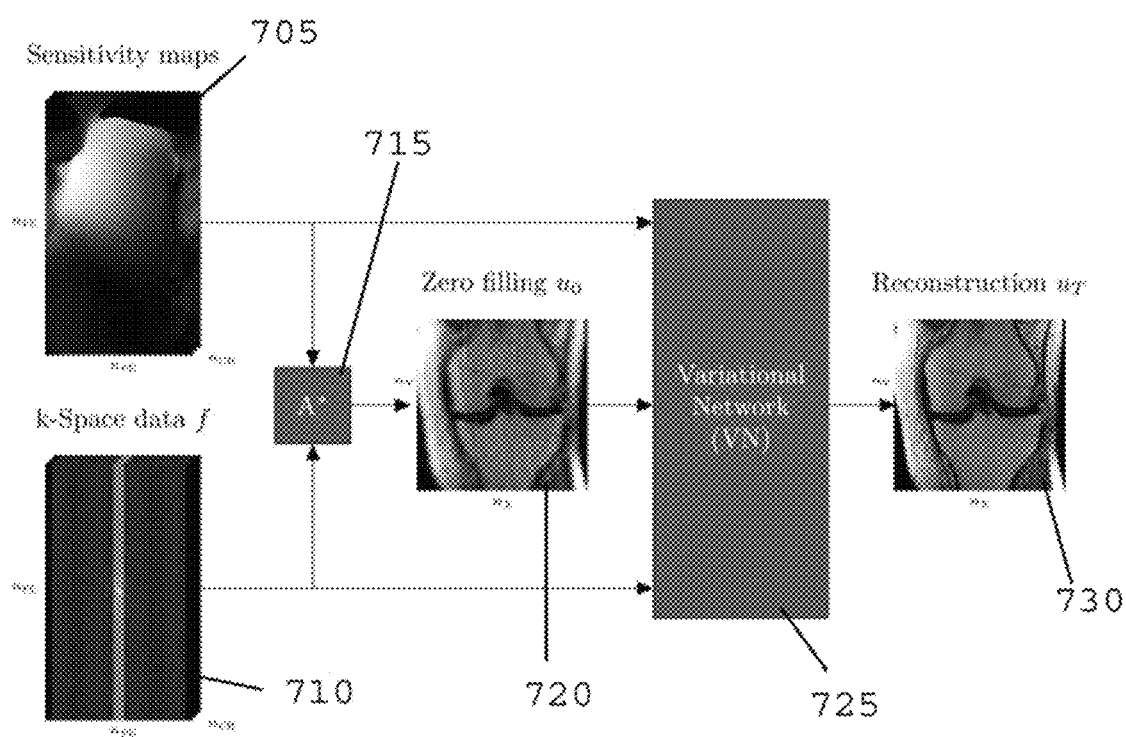
FIG. 7 is an exemplary flow diagram illustrating the data processing structure with a variational network for the exemplary system, method and computer-accessible medium, according to an exemplary embodiment of the present disclosure.

The exemplary data processing structure and flow diagram with the exemplary variational network is shown in the diagram shown in FIG. 7. The exemplary inputs of the exemplary variational network 725 (e.g., initializing of the exemplary system, method and computer-accessible medium), can include sensitivity maps 705, k-space data 710, and zero-filling 720. The zero-filling initialization can be obtained by application of the adjoint of the system matrix A* to the k-space data. In the example shown in FIG. 7, A* is comprised of an inverse Fourier transform of the data from each receive channel, point-wise multiplication of the individual images with the adjoint of the coil sensitivity map of that particular channel, and a finally a summation over the channels. The exemplary output can include a reconstruction image 730 having a superior quality to previously-reconstructed images.

Figure 8:
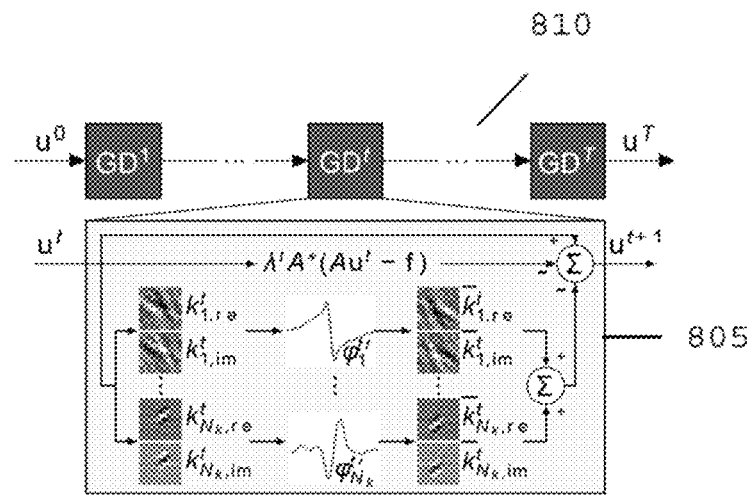
FIG. 8 is a further exemplary diagram illustrating the variational network structure of the exemplary system, method and computer-accessible medium, according to an exemplary embodiment of the present disclosure.

The variational network approach is shown in the diagram of FIG. 8. To reconstruct an image u, the image u0=A$^T$f can be propagated through T gradient descent ("GD") procedures 810 of the network. During a training process, optimal filter kernels $k_t i$ 805 can be used to influence functions $\Phi^n i$ and the regularization parameter $\lambda_t$ can be learned for each updated procedure. The exemplary network can be designed with filters for real and imaginary parts of complex numbers, for use with, for example, the complex nature of MR data.

The trainable gradient descent scheme with varying parameters can be defined as, for example:

$$u^{t+1} = u^t - \sum_{i=1}^{N_k} (K_i^t)^T \Phi_i^U (K_i^t u^t) - \lambda^t A^* (A u^t - f), \quad 0 \le t \le T - 1 \tag{6}$$

In Eq. (6) $\mu$ can be the current image estimate, f can be the measured MRI raw data and A can be the operator that can map between data space and image space and can include information about coil sensitivities and the data acquisition pattern. K, $\phi$ and $\lambda$ can be trainable parameters. $N_k$ can be the total number of filter kernels in each stage, and T can be the number of stages in the network.

Figure 9:
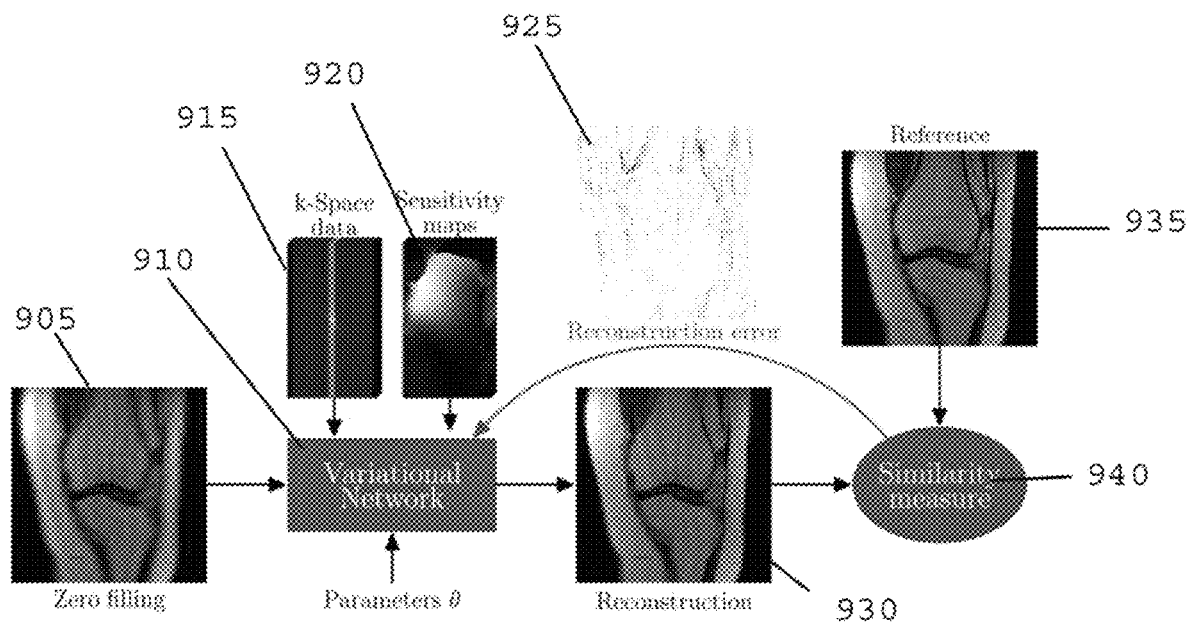
FIG. 9 is an exemplary flow diagram illustrating an exemplary training procedure used in the exemplary system, method and computer-accessible medium, according to an exemplary embodiment of the present disclosure.

The exemplary training procedure is shown in the exemplary diagram of FIG. 9. For example, as shown in FIG. 9, zero-filling 905, k-space data 915, and sensitivity maps 920 can be input into the exemplary variational network 910. A reconstructed image 930, having a reconstruction error 925, can be produced. An exemplary set of parameters of the exemplary network can be learned by comparing the current reconstruction 930 of the exemplary network to an artifact-free reference 935 using an exemplary similarity measure 940. Examples for similarity measures can be the pixel-wise mean-squared error or the structural similarity index. This can provide the reconstruction error, which can be propagated back to the network to compute a new set of parameters.

Figure 10:
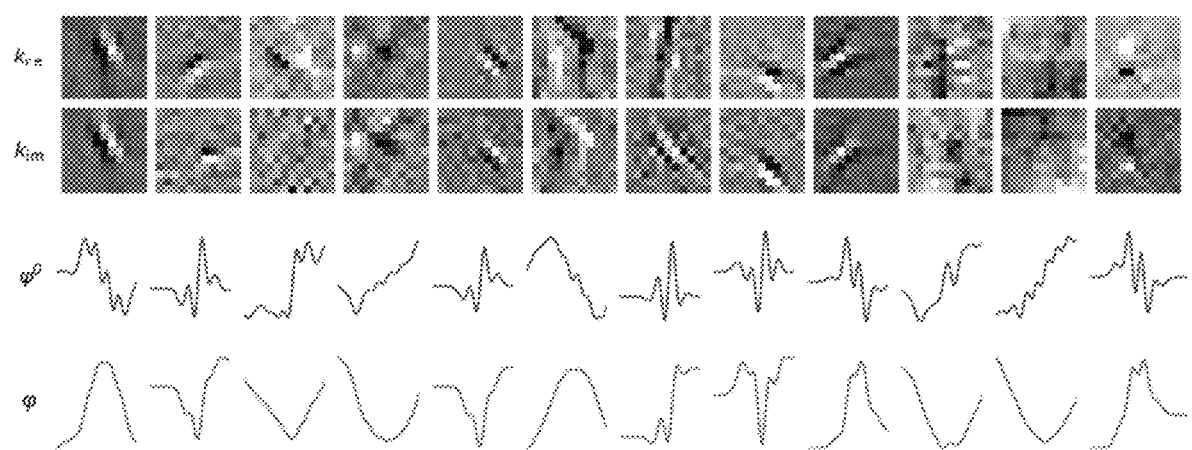
FIG. 10 is a set of exemplary images and corresponding learned parameters for the exemplary system, method and computer-accessible medium, according to an exemplary embodiment of the present disclosure.

The exemplary approach can facilitate insight in the operation of the network. This can be beneficial when operating in a critical environment like healthcare to understand the characteristics of the results. A subset of learned filter kernels and influence functions obtained with the exemplary network architecture and training procedure for MR image reconstruction is shown in FIG. 10. Filter kernels for the real ("kRE") and imaginary ("kIM") plane, as well as their corresponding activation function $\Phi'$ and potential function $\Phi$ are shown therein.

The exemplary functions can be computed by integrating the learned activation functions and can facilitate a better interpretation since they can be linked to the norms that can be used in the regularization terms of CS. Some of the learned filter pairs can have the same structure in both the real and imaginary plane, while some of them seem to be inverted in the real and imaginary part. In general, the filters in both the real and imaginary part show different (e.g., higher-order) derivative filters of various scales and orientations. Some of the learned potential functions in can be very close to the convex l1 norm used in CS, but substantial deviations can also be observed. When comparing these to the previous systems, functions with student-t characteristics can be identified, which can be reported to represent the statistics of natural images better than, for example, the l1-norm. (See e.g. Reference 24). The exemplary functions have been associated with image sharpening in the literature (See e.g. Reference 25).

The exemplary system, method and computer-accessible medium, according to an exemplary embodiment of the present disclosure, can be used to reconstruct images rooted in machine learning and computer vision that can provide a solution to these issues. Currently, new image reconstruction procedures can be performed as if there is no information about the imaged anatomy. By reformulating image reconstruction as an optimized variational network, a complete reconstruction procedure can be learned, including filter kernels and influence functions, to separate between true image content and artifacts, all parameters that normally have to be tuned manually as well as the associated numerical procedure. The exemplary training procedure can be decoupled from the time critical image reconstruction procedure, which can then be performed in near real time without interruption of clinical workflow.

Figure 11:
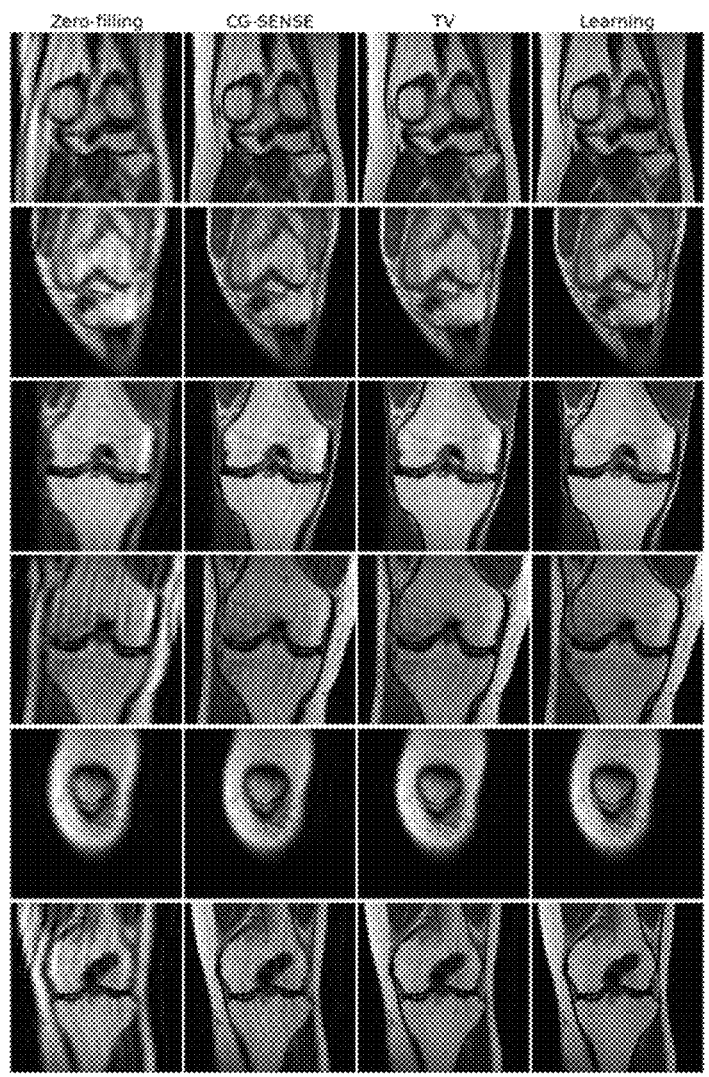
FIG. 11 is a set of exemplary images comparing reconstruction procedures for an acceleration factor of r=6.

FIG. 11 shows a set of exemplary images illustrating a comparison of the exemplary selected slices from 6 different patients undergoing knee MRI exams. The data acquisition was accelerated by a factor of 6 in comparison to a conventional acquisition. Results can be compared to one of the current standards in clinical practice, CG-SENSE (see e.g. reference 26), as well as one of the current standards in research, TV based combined parallel imaging and compressed sensing. (See e.g. Reference 14). Conventional zero filling results can also be shown to illustrate the amount of aliasing artifacts generated at this level of acceleration.

Figure 12:
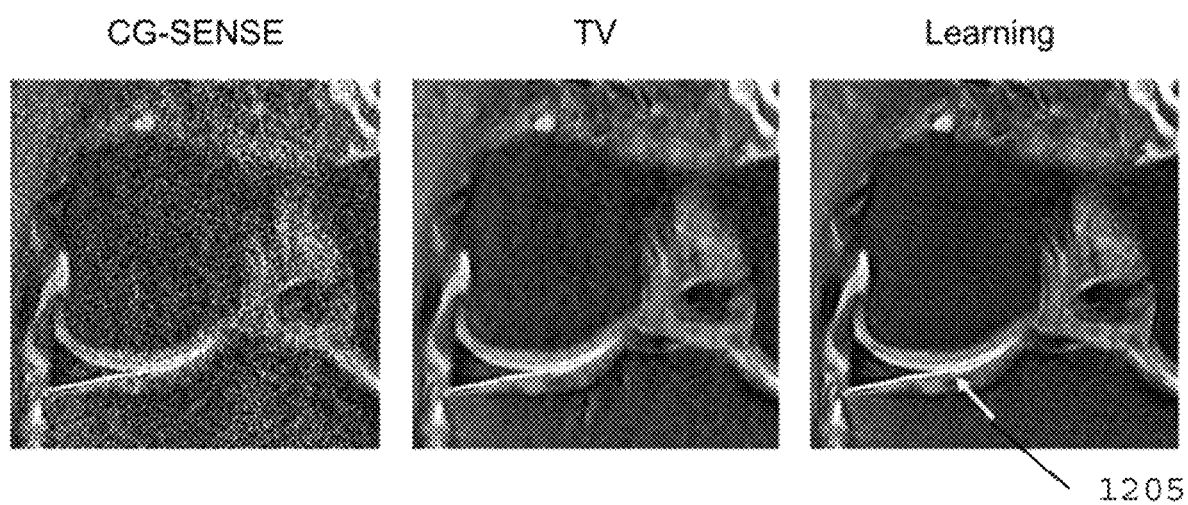
FIG. 12 is a set of exemplary images comparing reconstruction procedures for an acceleration factor of r=4.

FIG. 12 shows a set of exemplary images zoomed into the region of interest of a very subtle pathology, a fissure in the tibial cartilage, a type of pathology, which was not included in the training set. The data acquisition was accelerated by a factor of 4 in comparison to a conventional acquisition. A zoom into the region of interest of a subtle pathology, a fissure in the tibial cartilage (e.g., arrow 1205), is shown. CG-SENSE (see e.g. reference 26) and CS using TV (see e.g. reference 25 and 26) show substantial noise amplification and residual aliasing artifacts, while the results of the exemplary system, method, and computer-accessible medium are artifact free. In addition, the TV result exhibits the characteristic blocky appearance caused by the handcrafted regularization functional, as well as a slightly blurrier appearance with loss of small low contrast structures. The results show improved depiction with the proposed variational network for image reconstruction.

In contrast to prior accelerated reconstruction methods like compressed sensing, the regularization functions that separate artifacts from true image content can be specifically learned instead of using handcrafted and fixed sparsifying transforms. Instead of relying purely on artifact incoherence, which utilizes major modifications to the data acquisition strategy, the exemplary system, method, and computer-accessible medium can be directly applied to data from conventional parallel imaging based acquisition procedures. As a result, clinical translation of the exemplary system, method, and computer-accessible medium can be significantly easier than for compressed sensing based methods.

In contrast to neural networks for image restoration (see e.g. reference 16), the exemplary network can be designed such that the input can be raw measurement data, and information about coil sensitivities, and the output can be the reconstructed image. Thus, information about the specific imaging acquisition physics can be included in the training, which can then be used to learn the structure the introduced artifacts that have to be removed.

The exemplary variational network can be designed such that it can deal with complex numbers, which can be needed to process MM data. This can be beneficial when compared to learning-based methods for image restoration (see e.g. reference 16), which do not have to deal with complex data.

The exemplary system, method, and computer-accessible medium can have the accelerated MR imaging closer to daily clinical practice in areas that can be untouched by recent developments. This can reduce overall exam times, increases patient compliance and has the potential to reduce general healthcare costs.

Exemplary advantages of the exemplary system, method and computer-accessible medium, can be that (i) reconstructed images can have a more natural appearance and less artifacts than current state of the art compressed sensing reconstructions and (ii) faster data acquisition, which can lead to increased patient compliance, reduced motion artifacts and higher throughput, which can all lead to reduced healthcare costs.

In particular, according to the exemplary preliminary data from clinical 2D knee protocols, data acquisition can be performed 6-times accelerated in comparison to a fully sampled scan. By inspecting the influence functions and filter kernels of the learned variational network, the proposed approach has additional potential as a discovery tool for sparsifying transforms and numerical methods for regular compressed sensing type reconstructions.

Exemplary Results

For evaluation, the learned network was applied to R=2 and R=6 data from 6 patients that was not used for training, covering a wide range of anatomical knee structures. The exemplary system, method, and computer-accessible medium was compared to zero-filled initialization, iterative CG-SENSE (see, e.g., Reference 12) and TV-regularized combined CS and PI (see, e.g., Reference 2) reconstructions. FIG. 3 depicts images of the results for R=2. As expected, all methods perform equally well. When the acceleration factor can be pushed to R=6, CG-SENSE, TV cannot remove all artifacts as illustrated in FIG. 4. This is also illustrated in FIG. 4, which illustrates several reconstructed slices of a single patient. Although TV-regularized reconstructions can still include residual aliasing at this level of regularization, they can already look unnatural due to the piecewise-constancy assumption, and the small low-contrast features vanish. The exemplary system, method and computer-accessible medium, according to an exemplary embodiment of the present disclosure, can provide artifact-free and natural results with a reconstruction time of about 1.78 seconds for a single 320×320 slice.

Figure 13:
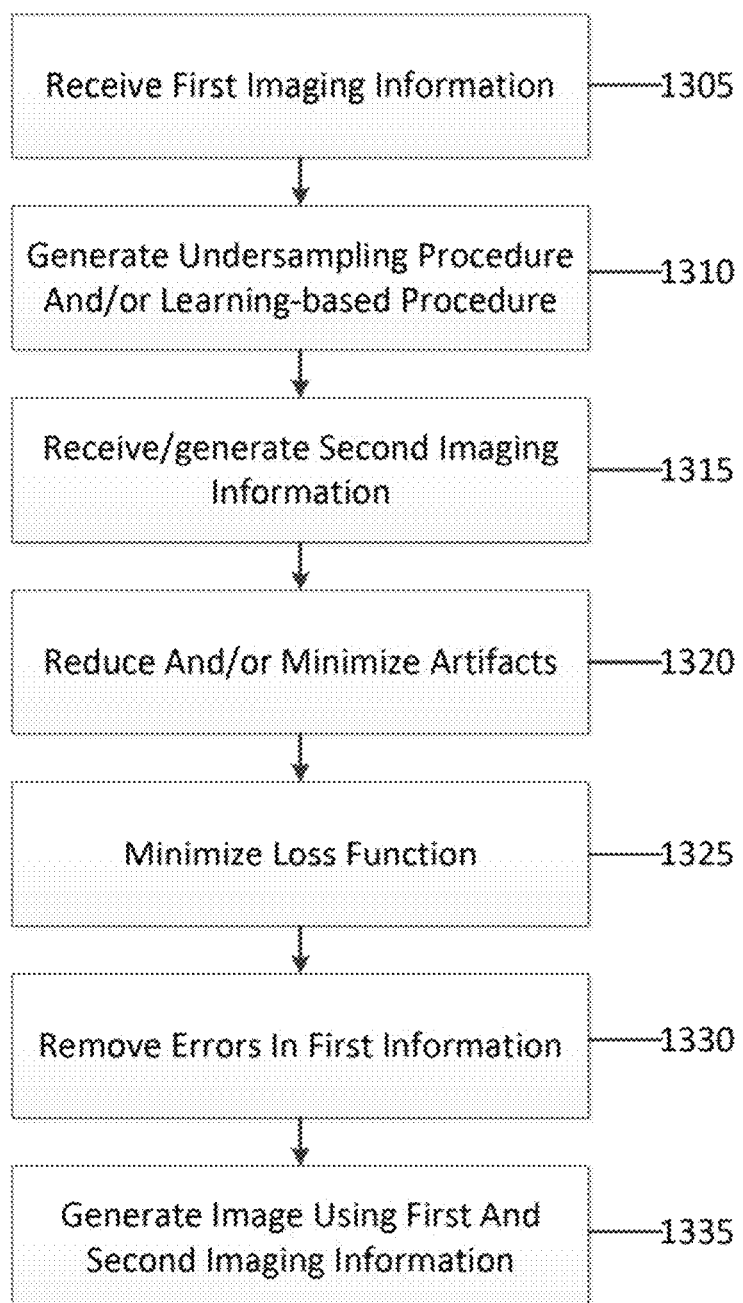
FIG. 13 is an exemplary flow diagram of an exemplary method for generating an image of a portion of a patient according to an exemplary embodiment of the present disclosure.

FIG. 13 shows an exemplary flow diagram 1300 of an exemplary method for generating an image of a portion of a patient according to an exemplary embodiment of the present disclosure. For example, at procedure 1305, first imaging information related to a portion of a patient can be received. At procedure 1310, an undersampling procedure and/or a learning-based procedure can be generated, which can be used to generate the second imaging information at procedure 1315. Alternatively, the second information can be received at procedure 1315. At procedure 1320, artifacts in the first imaging information can be reduced or minimized. At procedure 1325, a loss function in the first imaging information can be minimized. At procedure 1330, errors in the first information can be removed. The image of the portion of the patient can be generated at procedure 1335 by applying the second imaging information to the first imaging information. Some or all of procedures 1320-1330 can be performed using the second imaging information.

Figure 14:
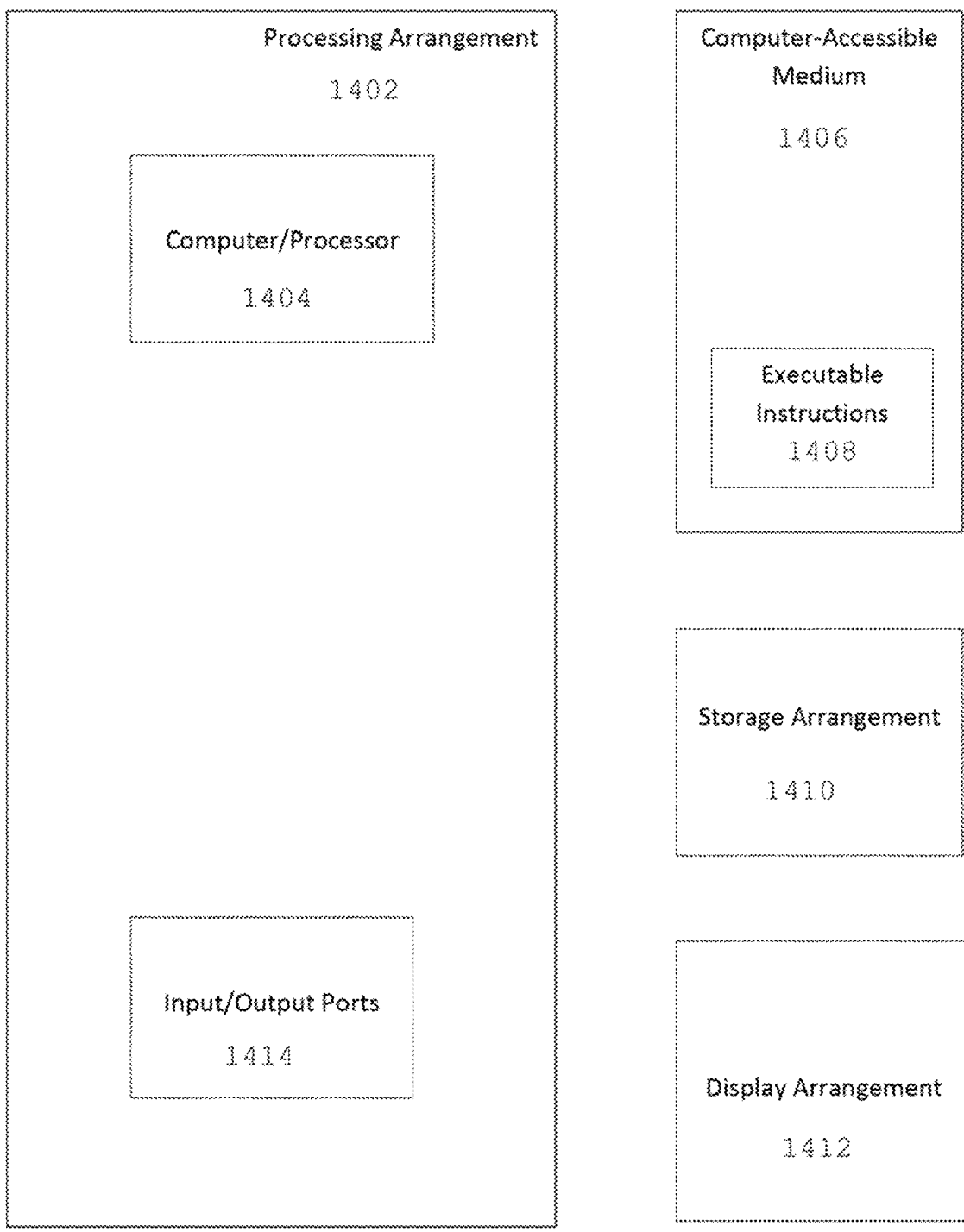
FIG. 14 is an illustration of an exemplary block diagram of an exemplary system in accordance with certain exemplary embodiments of the present disclosure.

FIG. 14 shows a block diagram of an exemplary embodiment of a system according to the present disclosure. For example, exemplary procedures in accordance with the present disclosure described herein can be performed by a processing arrangement and/or a computing arrangement 1402. Such processing/computing arrangement 1402 can be, for example entirely or a part of, or include, but not limited to, a computer/processor 1404 that can include, for example one or more microprocessors, and use instructions stored on a computer-accessible medium (e.g., RAM, ROM, hard drive, or other storage device).

As shown in FIG. 14, for example a computer-accessible medium 1406 (e.g., as described herein above, a storage device such as a hard disk, floppy disk, memory stick, CD-ROM, RAM, ROM, etc., or a collection thereof) can be provided (e.g., in communication with the processing arrangement 1402). The computer-accessible medium 1406 can contain executable instructions 1408 thereon. In addition or alternatively, a storage arrangement 1410 can be provided separately from the computer-accessible medium 1406, which can provide the instructions to the processing arrangement 1402 so as to configure the processing arrangement to execute certain exemplary procedures, processes and methods, as described herein above, for example.

Further, the exemplary processing arrangement 1402 can be provided with or include an input/output arrangement 1414, which can include, for example a wired network, a wireless network, the internet, an intranet, a data collection probe, a sensor, etc. As shown in FIG. 14, the exemplary processing arrangement 1402 can be in communication with an exemplary display arrangement 1412, which, according to certain exemplary embodiments of the present disclosure, can be a touch-screen configured for inputting information to the processing arrangement in addition to outputting information from the processing arrangement, for example. Further, the exemplary display 1412 and/or a storage arrangement 1410 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.

1. M. Lustig, D. Donoho, and J. M. Pauly, "Sparse Mill: The application of compressed sensing for rapid MR imaging." *Magn Reson Med*, vol. 58, no. 6, pp. 1182-1195, December 2007.
2. K. T. Block, M. Uecker, and J. Frahm, "Undersampled radial MRI with multiple coils. Iterative image reconstruction using a total variation constraint." Magn Reson Med, vol. 57, no. 6, pp. 1086-1098, June 2007.
3. D. Ma, V. Gulani, N. Seiberlich, K. Liu, J. L. Sunshine, J. L. Duerk, and M. A. Griswold, "Magnetic resonance fingerprinting." *Nature, vol.* 495, no. 7440, pp. 187-192, March 2013.
4. Y. Chen, W. Yu, and T. Pock, "On learning optimized reaction diffusion processes for effective image restoration," in *IEEE Conference on Computer Vision and Pattern Recognition (CVPR)*, pp. 5261-5269, 2015.
5. B. Bilgic, V. K. Goyal, and E. Adalsteinsson, "Multi-contrast reconstruction with Bayesian compressed sensing." Magn Reson Med, vol. 66, no. 6, pp. 1601-1615, December 2011.
6. K. T. Block, M. Uecker, and J. Frahm, "Model-based iterative reconstruction for radial fast spin-echo MRI." *IEEE Trans Med Imaging*, vol. 28, no. 11, pp. 1759-1769, November 2009.
7. M. Doneva, P. Boernert, H. Eggers, C. Stehning, J. Senegas, and A. Mertins, "Compressed sensing reconstruction for magnetic resonance parameter mapping." *Magn Reson Med*, vol. 64, no. 4, pp. 1114-1120, October 2010.
8. T. J. Sumpf, A. Petrovic, M. Uecker, F. Knoll, and J. Frahm, "Fast t2 mapping with improved accuracy using undersampled spin-echo mri and model-based reconstructions with a generating function." *IEEE Trans Med Imaging*, vol. 33, no. 12, pp. 2213-2222, December 2014.
9. S. L. Keeling, M. Hintermueller, F. Knoll, D. Kraft, A. Laurain, "A total variation based approach to correcting surface coil magnetic resonance images," in *Applied Mathematics and Computation*, vol. 218, no. 2, pp. 219-232, September 2011.
10. D. K. Sodickson, L. Feng, F. Knoll, M. Cloos, N. Ben-Eliezer, L. Axel, H. Chandarana, T. Block, and R. Otazo, "The rapid imaging renaissance: sparser samples, denser dimensions, and glimmerings of a grand unified tomography," vol. 9417, pp. 94 170G-94 170G-14, 2015.
11. M. Cloos, T. Zhao, F. Knoll, L. Alon, R. Lattanzi, and D. Sodickson, "Magnetic resonance fingerprint compression," in *Proc. Intl. Soc. Mag. Reson. Med.*, no. 23, p. 330, 2015.
12. K. P. Pruessmann, M. Weiger, P Boernert and P Boesiger. Advances in sensitivity encoding with arbitrary k-space trajectories. *Magn Reson Med*, vol. 46, no. 4, pp. 638-651, October 2001.
13. M. Lustig, D. Donoho, and J. M. Pauly, "Sparse M M: The application of compressed sensing for rapid MR imaging." Magn Reson Med, vol. 58, no. 6, pp. 1182-1195 (2007).
14. K. T. Block, M. Uecker, and J. Frahm, "Undersampled radial MRI with multiple coils. Iterative image reconstruction using a total variation constraint." Magn Reson Med, vol. 57, no. 6, pp. 1086-1098 (2007).
15. D. Ma, V. Gulani, N. Seiberlich, K. Liu, J. L. Sunshine, J. L. Duerk, and M. A. Griswold, "Magnetic resonance fingerprinting." Nature, vol. 495, no. 7440, pp. 187-192 (2013).
16. Y. Chen, W. Yu, and T. Pock, "On learning optimized reaction diffusion processes for effective image restoration," in IEEE Conference on Computer Vision and Pattern Recognition (CVPR), pp. 5261-5269, (2015).
17.
18. B. Bilgic, V. K. Goyal, and E. Adalsteinsson, "Multi-contrast reconstruction with Bayesian compressed sensing." Magn Reson Med, vol. 66, no. 6, pp. 1601-1615 (2011).
19. K. T. Block, M. Uecker, and J. Frahm, "Model-based iterative reconstruction for radial fast spin-echo Mill." IEEE Trans Med Imaging, vol. 28, no. 11, pp. 1759-1769 (2009).
20. M. Doneva, P. Boernert, H. Eggers, C. Stehning, J. Senegas, and A. Mertins, "Compressed sensing reconstruction for magnetic resonance parameter mapping." Magn Reson Med, vol. 64, no. 4, pp. 1114-1120 (2010).
21. T. J. Sumpf, A. Petrovic, M. Uecker, F. Knoll, and J. Frahm, "Fast t2 mapping with improved accuracy using undersampled spin-echo mri and model-based reconstructions with a generating function." IEEE Trans Med Imaging, vol. 33, no. 12, pp. 2213-2222 (2014).
22. S. L. Keeling, M. Hintermueller, F. Knoll, D. Kraft, A. Laurain, "A total variation based approach to correcting surface coil magnetic resonance images," in Applied Mathematics and Computation, vol. 218, no. 2, pp. 219-232 (2011).
23. D. K. Sodickson, L. Feng, F. Knoll, M. Cloos, N. Ben-Eliezer, L. Axel, H. Chandarana, T. Block, and R. Otazo, "The rapid imaging renaissance: sparser samples, denser dimensions, and glimmerings of a grand unified tomography," vol. 9417, pp. 94 170G-94 170G-14 (2015).
24. M. Cloos, T. Zhao, F. Knoll, L. Alon, R. Lattanzi, and D. Sodickson, "Magnetic resonance fingerprint compression," in Proc. Intl. Soc. Mag. Reson. Med., no. 23, p. 330 (2015).
25. Huang J H J, Mumford D. Statistics of Natural Images and Models. In Proceedings of the IEEE Conference on Computer Vision and Pattern Recognition. 541-547 (1999).
26. Zhu S C, Mumford D. Prior Learning and Gibbs Reaction-Diffusion. IEEE Transactions on Pattern Analysis and Machine Intelligence. 19:1236-1250 (1997).
27. K. P. Pruessmann, M. Weiger, P Boernert and P Boesiger. Advances in sensitivity encoding with arbitrary k-space trajectories. Magn Reson Med, vol. 46, no. 4, pp. 638-651 (2001).

What is claimed is:

1. A non-transitory computer-accessible medium having stored thereon computer-executable instructions for generating at least one image of at least one portion of a patient, wherein, when a computer arrangement executes the instructions, the computer arrangement is configured to perform procedures comprising:
receiving first imaging information related to the at least one portion;
receiving second information related to modelling information of at least one further portion of at least one further patient, wherein the modelling information includes at least one of (i) an under sampling procedure, or (ii) a learning-based procedure;
removing errors in the first imaging information using the second information; and
automatically generating the at least one image using the first information and the second information.

2. The computer-accessible medium of claim 1, wherein the modelling information includes artifacts present in a further image of the at least one further portion.

3. The computer-accessible medium of claim 2, wherein the computer arrangement is configured to generate the at least one image by reducing or minimizing the artifacts.

4. The computer-accessible medium of claim 1, wherein the computer arrangement is further configured to generate the second information.

5. The computer-accessible medium of claim 4, wherein the computer-arrangement is configured to generate the second information using at least one variational network.

6. The computer-accessible medium of claim 5, wherein the at least one variational network is based on at least one gradient descent procedure.

7. The computer-accessible medium of claim 5, wherein the at least one variational network is based on a loss function.

8. The computer-accessible medium of claim 7, wherein the computer arrangement is configured to minimize the loss function over a set of training images of the at least one further portion.

9. The computer-accessible medium of claim 5, wherein the at least one of (i) the under sampling procedure, or (ii) the learning-based procedure includes filter kernels and corresponding influence functions of the at least one variational network.

10. The computer-accessible medium of claim 9, wherein the computer arrangement is further configured to automatically learn the filter kernels and influence functions by optimizing a loss function that compares under sampled, aliased, images to artifact-free reference reconstructions of the at least one portion.

11. The computer-accessible medium of claim 5, wherein the at least one variational network includes convolutional filters in at least one of a real plane or an imaginary plane.

12. The computer-accessible medium of claim 1, wherein the computer arrangement is further configured automatically generate the at least one image by applying the second imaging information to the first imaging information.

13. The computer-accessible medium of claim 1, wherein the computer arrangement is further configured to automatically generate the at least one of (i) the under sampling procedure, or (ii) the learning-based procedure.

14. The computer-accessible medium of claim 13, wherein the computer arrangement is configured to generate the at least one of (i) the under sampling procedure, or (ii) the learning-based procedure by using information about a pattern in k-space in the second imaging information to discriminate aliasing artifacts.

15. The computer-accessible medium of claim 14, wherein the aliasing artifacts are based on under sampling from true anatomical structures.

16. The computer-accessible medium of claim 13, wherein the computer arrangement is configured to automatically generate the at least one of (i) the under sampling procedure, or (ii) the learning-based procedure based on coil sensitivities and raw k-space measurements.

17. The computer-accessible medium of claim 1, wherein at least one of the first imaging information or the second imaging information includes at least one of (i) magnetic resonance imaging information, (ii) computed tomography imaging information, (iii) positron emission tomography imaging information, or (iv) optical imaging information.

18. A system for generating at least one image of at least one portion of a patient, comprising:
at least one computer hardware arrangement configured to:
receive first imaging information related to the at least one portion;
receive second information related to modelling information of at least one further portion of at least one further patient, wherein the modelling information includes at least one of (i) an under sampling procedure, or (ii) a learning-based procedure;
remove errors in the first imaging information using the second information; and
generate the at least one image using the first information and the second information.

19. The system of claim 18, wherein the modelling information includes artifacts present in a further image of the at least one further portion.

20. The system of claim 19, wherein the computer hardware arrangement is configured to generate the at least one image by reducing or minimizing the artifacts.

21. The system of claim 18, wherein the computer arrangement is further configured automatically generate the at least one image by applying the second imaging information to the first imaging information.

22. A method for generating at least one image of at least one portion of a patient, comprising:
receiving first imaging information related to the at least one portion;
receiving second information related to modelling information of at least one further portion of at least one further patient, wherein the modelling information includes at least one of (i) an under sampling procedure, or (ii) a learning-based procedure;
removing errors in the first imaging information using the second information; and
using a computer hardware arrangement, generating the at least one image using the first information and the second information.

23. The method of claim 22, wherein the modelling information includes artifacts present in a further image of the at least one further portion.

24. The method of claim 23, wherein the generating the at least one image using the first information and the second information includes reducing or minimizing the artifacts.

25. The method of claim 22, wherein the generating the at least one image includes applying the second imaging information to the first imaging information.

26. A non-transitory computer-accessible medium having stored thereon computer-executable instructions for generating at least one image of at least one portion of a patient, wherein, when a computer arrangement executes the instructions, the computer arrangement is configured to perform procedures comprising:
receiving first imaging information related to the at least one portion;
receiving second information related to modelling information of at least one further portion of at least one further patient, wherein the modelling information includes artifacts present in a further image of the at least one further portion, and at least one of (i) an under sampling procedure, or (ii) a learning-based procedure; and
automatically generating the at least one image using the first information and the second information.

27. The computer-accessible medium of claim 26, wherein the computer arrangement is configured to generate the at least one image by reducing or minimizing the artifacts.

28. The computer-accessible medium of claim 26, wherein the computer arrangement is further configured automatically generate the at least one image by applying the second imaging information to the first imaging information.

29. A system for generating at least one image of at least one portion of a patient, comprising:
at least one computer hardware arrangement configured to:
receive first imaging information related to the at least one portion;
receive second information related to modelling information of at least one further portion of at least one further patient, wherein the modelling information includes artifacts present in a further image of the at least one further portion, and at least one of (i) an under sampling procedure, or (ii) a learning-based procedure; and
generate the at least one image using the first information and the second information.

30. The system of claim 29, wherein the computer hardware arrangement is configured to generate the at least one image by reducing or minimizing the artifacts.

31. The computer-accessible medium of claim 29, wherein the computer hardware arrangement is further configured automatically generate the at least one image by applying the second imaging information to the first imaging information.

32. A method for generating at least one image of at least one portion of a patient, comprising:
receiving first imaging information related to the at least one portion;
receiving second information related to modelling information of at least one further portion of at least one further patient, wherein the modelling information includes artifacts present in a further image of the at least one further portion, and at least one of (i) an under sampling procedure, or (ii) a learning-based procedure; and using a computer hardware arrangement, generating the at least one image using the first information and the second information.

33. The method of claim 32, wherein the generating the at least one image using the first information and the second information includes reducing or minimizing the artifacts.

34. The method of claim 32, wherein the generating the at least one image using the first information and the second information includes applying the second imaging information to the first imaging information.

* * * * *